(12) United States Patent
Knott et al.

(10) Patent No.: US 12,194,222 B2
(45) Date of Patent: *Jan. 14, 2025

(54) TEMPERATURE CONTROL DEVICE FOR FLUID-BASED HYPER/HYPOTHERMIA SYSTEMS

(71) Applicant: LivaNova Deutschland GmbH, Munich (DE)

(72) Inventors: Erwin Knott, Poing (DE); Manfred Fronhöfer, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 700 days.

This patent is subject to a terminal disclaimer.

(21) Appl. No.: 17/313,781

(22) Filed: May 6, 2021

(65) Prior Publication Data

US 2021/0259876 A1  Aug. 26, 2021

Related U.S. Application Data

(63) Continuation of application No. 15/703,292, filed on Sep. 13, 2017, now Pat. No. 11,026,833, which is a
(Continued)

(30) Foreign Application Priority Data

Apr. 8, 2011  (DE) .......................... 102011016508.8

(51) Int. Cl.
A61F 7/00  (2006.01)
A61M 1/36  (2006.01)

(52) U.S. Cl.
CPC .......... *A61M 1/369* (2013.01); *A61F 7/0085* (2013.01); *A61F 2007/0078* (2013.01);
(Continued)

(58) Field of Classification Search
CPC ..................................................... A61F 7/0085
See application file for complete search history.

(56) References Cited

U.S. PATENT DOCUMENTS 3,064,649 A  11/1962  Fuson
3,614,534 A  10/1971  Gross
(Continued)

FOREIGN PATENT DOCUMENTS

AU  768251 B2  12/2003
CN  1202116 A  12/1998
(Continued)

OTHER PUBLICATIONS

International Preliminary Report on Patentability issued in PCT/EP2012/056154, completed Aug. 13, 2013, 10 pages.
(Continued)

*Primary Examiner* — Kaitlyn E Smith
(74) *Attorney, Agent, or Firm* — Seager, Tufte & Wickhem LLP

(57) ABSTRACT

Temperature control device for use in fluid-based hyper/hypothermia systems, comprising a connection unit for connecting the device to a local power network, and a fluid temperature control unit for heating or cooling a fluid. The device includes a power supply unit, by which electrical consuming components of the fluid temperature control unit are supplied with power, and which effects supply of the electrical consuming components with direct current.

16 Claims, 2 Drawing Sheets

Related U.S. Application Data continuation of application No. 14/147,764, filed on Jan. 6, 2014, now abandoned, which is a continuation of application No. 13/441,603, filed on Apr. 6, 2012, now Pat. No. 9,351,869.

(52) U.S. Cl.
CPC . *A61M 2205/3368* (2013.01); *A61M 2205/36* (2013.01); *A61M 2205/82* (2013.01); *A61M 2205/8206* (2013.01); *F04C 2270/041* (2013.01)

(56) References Cited

U.S. PATENT DOCUMENTS

| | | | |
|---|---|---|---|
| 4,180,896 A | 1/1980 | Cooley et al. | |
| 4,221,543 A | 9/1980 | Cosentino | |
| 4,231,425 A | 11/1980 | Engstrom | |
| 4,298,006 A | 11/1981 | Parks | |
| 4,517,633 A | 5/1985 | Melcher | |
| 4,966,145 A | 10/1990 | Kikumoto et al. | |
| 5,019,076 A | 5/1991 | Yamanashi et al. | |
| 5,117,834 A | 6/1992 | Kroll et al. | |
| 5,242,404 A | 9/1993 | Conley et al. | |
| 5,247,434 A | 9/1993 | Peterson et al. | |
| 5,409,612 A | 4/1995 | Maltais et al. | |
| 5,487,827 A | 1/1996 | Peterson et al. | |
| 5,647,984 A | 7/1997 | Hovland et al. | |
| 5,730,720 A | 3/1998 | Sites et al. | |
| 5,863,501 A | 1/1999 | Cosentino | |
| 5,871,526 A | 2/1999 | Gibbs | |
| 5,900,256 A | 5/1999 | Scoville, Jr. et al. | |
| 6,117,164 A | 9/2000 | Gildersleeve et al. | |
| 6,156,007 A | 12/2000 | Ash | |
| 6,175,688 B1 | 1/2001 | Cassidy et al. | |
| 6,581,403 B2 | 6/2003 | Whitebook et al. | |
| 6,635,076 B1 | 10/2003 | Ginsburg | |
| 6,655,394 B1 | 12/2003 | Tanaka et al. | |
| 6,891,136 B2 | 5/2005 | Bikovsky et al. | |
| 6,939,347 B2 | 9/2005 | Thompson | |
| 6,981,794 B2 | 1/2006 | Bibbo et al. | |
| 7,094,231 B1 * | 8/2006 | Ellman | A61B 18/1206 606/34 |
| 7,176,419 B2 | 2/2007 | Ellis et al. | |
| 7,220,260 B2 | 5/2007 | Fleming et al. | |
| 7,900,629 B2 | 3/2011 | Gurnee et al. | |
| 8,231,664 B2 | 7/2012 | Kulstad et al. | |
| 8,308,787 B2 | 11/2012 | Kreck | |
| 8,343,202 B2 | 1/2013 | Magers | |
| 8,475,509 B2 | 7/2013 | Dae | |
| 9,259,523 B2 | 2/2016 | Schreyer et al. | |
| 9,351,869 B2 * | 5/2016 | Knott | A61M 1/369 |
| 9,927,416 B2 | 3/2018 | Schreyer et al. | |
| 9,956,308 B2 | 5/2018 | Schreyer et al. | |
| 2003/0060864 A1 | 3/2003 | Whitebook et al. | |
| 2004/0068310 A1 | 4/2004 | Edelman | |
| 2004/0149711 A1 | 8/2004 | Wyatt et al. | |
| 2004/0267340 A1 | 12/2004 | Cioanta et al. | |
| 2005/0047959 A1 | 3/2005 | Brandl et al. | |
| 2005/0284815 A1 | 12/2005 | Sparks et al. | |
| 2007/0020142 A1 | 1/2007 | Federspiel et al. | |
| 2009/0012450 A1 | 1/2009 | Shah et al. | |
| 2009/0056344 A1 | 3/2009 | Poch | |
| 2009/0069731 A1 | 3/2009 | Parish et al. | |
| 2010/0030306 A1 | 2/2010 | Edelman et al. | |
| 2010/0106229 A1 | 4/2010 | Gammons et al. | |
| 2010/0143192 A1 | 6/2010 | Myrick et al. | |
| 2011/0107251 A1 | 5/2011 | Guaitoli et al. | |
| 2012/0167879 A1 | 7/2012 | Bowman et al. | |
| 2012/0259394 A1 | 10/2012 | Knott et al. | |
| 2012/0308431 A1 | 12/2012 | Kotsos et al. | |
| 2013/0079763 A1 | 3/2013 | Heckel et al. | |
| 2013/0116761 A1 | 5/2013 | Kreck | |
| 2013/0280692 A1 | 10/2013 | Gourlay | |
| 2013/0324619 A1 | 12/2013 | Chtourou | |
| 2013/0331739 A1 | 12/2013 | Gertner | |
| 2014/0014580 A1 | 1/2014 | Ritter | |
| 2014/0121734 A1 | 5/2014 | Knott et al. | |
| 2014/0308654 A1 | 10/2014 | Kay et al. | |
| 2015/0217014 A1 | 8/2015 | Schreyer et al. | |
| 2015/0265759 A1 | 9/2015 | Schreyer et al. | |
| 2016/0139100 A1 | 5/2016 | Schreyer et al. | |
| 2017/0216509 A1 | 8/2017 | Bellini | |
| 2017/0267907 A1 | 9/2017 | Knott et al. | |
| 2018/0243455 A1 | 8/2018 | Schreyer et al. | |

FOREIGN PATENT DOCUMENTS

| | | |
|---|---|---|
| CN | 201871012 U | 6/2011 |
| CN | 202154894 U | 3/2012 |
| CN | 102526822 A | 7/2012 |
| DE | 3883452 T2 | 1/1994 |
| DE | 19531935 A1 | 2/1997 |
| DE | 19924856 A1 | 12/2000 |
| DE | 69331840 T2 | 11/2002 |
| DE | 69634572 T2 | 2/2006 |
| EP | 0297723 A2 | 1/1989 |
| EP | 0555625 A1 | 8/1993 |
| EP | 0864334 A1 | 9/1998 |
| EP | 1267958 A2 | 1/2003 |
| EP | 1970080 A1 | 9/2008 |
| EP | 2698176 A1 | 2/2014 |
| EP | 2698177 B1 | 1/2015 |
| FR | 2631241 A1 | 11/1989 |
| FR | 2791574 A1 | 10/2000 |
| JP | S54154195 A | 12/1979 |
| JP | S61131753 A | 6/1986 |
| JP | H11057733 A | 3/1999 |
| JP | 2001506971 A | 5/2001 |
| JP | 2002539893 A | 11/2002 |
| JP | 2003260131 A | 9/2003 |
| JP | 2005074236 A | 3/2005 |
| JP | 2005514085 A | 5/2005 |
| JP | 2005219041 A | 8/2005 |
| JP | 2008111612 A | 5/2008 |
| JP | 2014503305 A | 2/2014 |
| WO | 9706840 A1 | 2/1997 |
| WO | 9811777 A1 | 3/1998 |
| WO | 0172352 A2 | 10/2001 |
| WO | 03054660 A2 | 7/2003 |
| WO | 2006063080 A1 | 6/2006 |
| WO | 2009094601 A2 | 7/2009 |
| WO | 2012090067 A1 | 7/2012 |
| WO | 2014026833 A1 | 2/2014 |

OTHER PUBLICATIONS

International Search Report and Written Opinion issued in PCT/EP056154. mailed Jun. 26, 2012, 9 pages.

Netzteil (English: Power Supply), downloaded from German Wikipedia on Apr. 5, 2011, with English Wikipedia translation downloaded on Dec. 23, 2013.

Schaltnetzteil (English: Switching Power Supply), downloaded from German Wikipedia on Mar. 30, 2011, with English Wikipedia translation downloaded on Dec. 23, 2013, 13 pages.

Extended European Search Report issued in EP Application 16195495.3, mailed Feb. 14, 2017, 9 pages.

* cited by examiner

TEMPERATURE CONTROL DEVICE FOR FLUID-BASED HYPER/HYPOTHERMIA SYSTEMS

CROSS-REFERENCE TO RELATED APPLICATION

This application is a continuation of U.S. application Ser. No. 15/703,292, filed Sep. 13, 2017, which is a continuation of U.S. application Ser. No. 14/147,764, filed Jan. 6, 2014, which is a continuation of U.S. application Ser. No. 13/441,603, filed Apr. 6, 2012, now U.S. Pat. No. 9,351,869, which claims priority to German Application No. 10 2011 016 508.8, filed Apr. 8, 2011, which are herein incorporated by reference in their entirety.

TECHNICAL FIELD

The invention relates to a temperature control device for use in fluid-based hyper/hypothermia systems.

BACKGROUND

A fluid-based hyper/hypothermia system is disclosed, for example, in DE 696 34 572 T2. Fluid-based hyper/hypothermia systems that use a temperature-controlled fluid to raise the temperature of a human or animal body, body part or organ to above the normal core body temperature or to lower it to below the normal core body temperature require a temperature control device that provides a temperature-controlled fluid to accomplish the desired change in body temperature. The temperature of the fluid must be controlled in the temperature control device in accordance with the quantity of heat to be supplied to or removed from the body. The fluid, for example, must be heated or cooled and then maintained at a predetermined temperature.

SUMMARY

In order to heat or cool the fluid in a temperature control device, energy is required that is provided as a general rule by the local power network. Thus, a conventional temperature control device comprises a power supply which allows the temperature control device to be connected to the local power network. Both the power supply as well as numerous individual electrical consuming components of the temperature control device must be adapted to the local power network. Since there are different local power networks in different regions of the world, the region of the world in which the temperature control device is ultimately supposed to be used and the specifications of the local power network according to which the power supply of the temperature control device and the temperature control device itself have to be configured must, with a considerable amount of effort, always be taken into consideration when constructing a temperature control device for hyper/hypothermia applications.

Various embodiments of the invention simplify the construction of a temperature control device and provide a temperature control device for hyper/hypothermia systems that can be used in different regions of the world. This aim is achieved by a temperature control device for use in fluid-based hyper/hypothermia systems, comprising: a connection unit for connecting the device to a local power network; and a fluid temperature control unit for heating or cooling a fluid including a power supply unit that supplies electrical consuming components of the fluid temperature control unit with power, and supplies the electrical consuming components with direct current.

DETAILED DESCRIPTION

Figure 1:
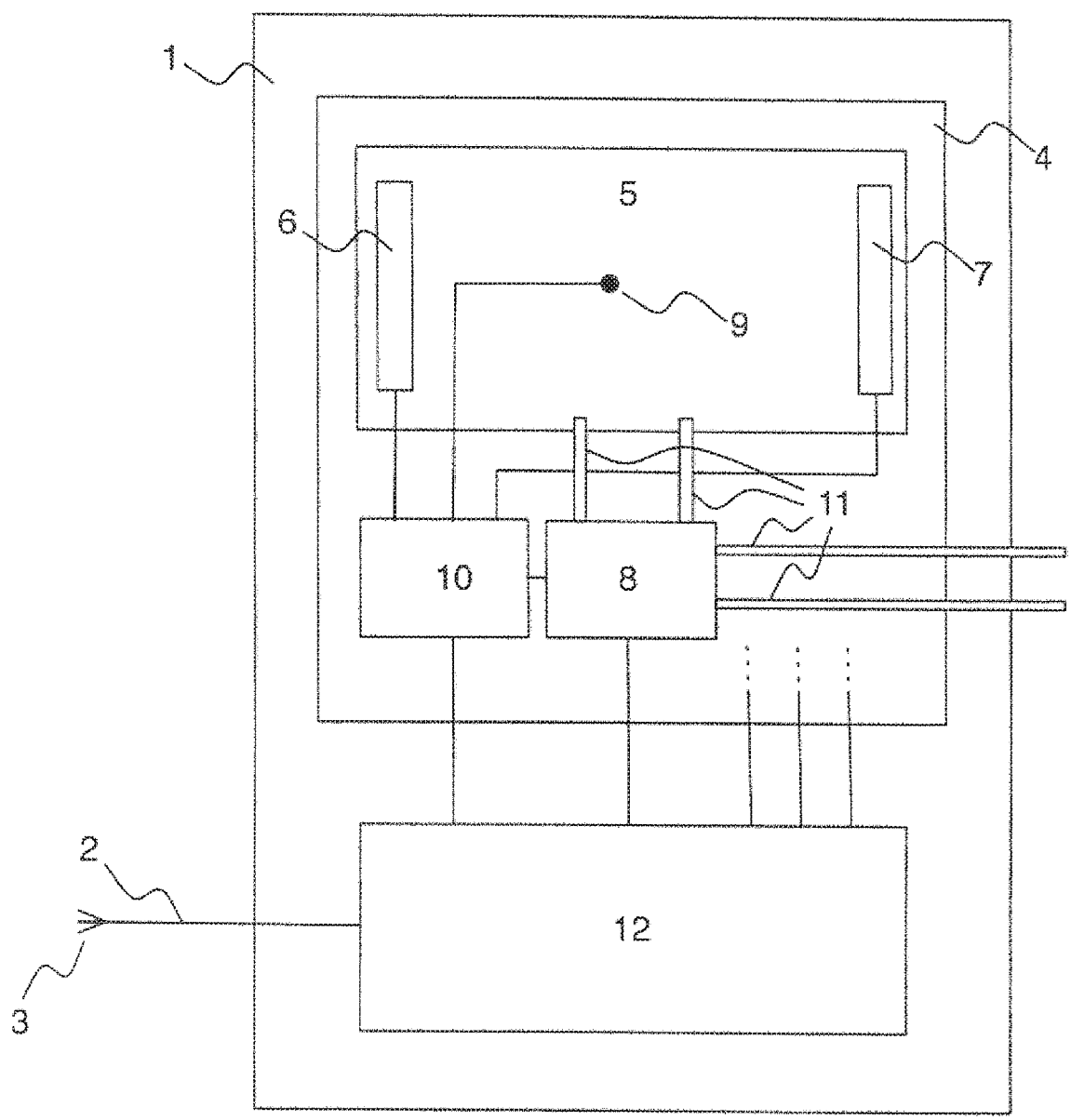
FIG. 1 shows an embodiment of a temperature control device according to the invention.

FIG. 1 shows a temperature control device 1 for use in a fluid-based hyperthermia or hypothermia system, according to embodiments of the invention. As shown in FIG. 1, the control device 1 includes a connection unit 2 for connecting the device to a local power network 3. In Germany, for example, the local power network is a general alternating current (AC) network of 220/380 V at 50 Hz. In Japan, for example, the local power network is an AC network of 100 V at, for example, 60 Hz. And in the United States, for example, the local power network is an AC network of 120 V at 60 Hz. These differences, and in particular the differences in frequency of the local power networks, lead to differences in the leakage currents which result from the change of the connected alternating current over time. For medical-technical systems in a surgical environment, the effects of electrical leakage currents, in the case for example of open heart surgeries, must remain minimal. To minimize these leakage currents, the electric lines in conventional temperature control devices must have certain insulations. This leads to increased material costs since, in particular, the insulation can age and must then be replaced if the guidelines with respect to the leakage currents are no longer met.

The temperature control device, according to the illustrative embodiments of the invention, is connected to the power network 3 via the connection unit 2 and can draw the power required to control the temperature of the fluid from the power network.

The temperature control of the fluid is accomplished by means of a fluid temperature control unit 4 which includes the components required for heating or cooling the fluid. These normally include a fluid container 5, a heater 6, a cooler 7, a supply pump 8, a temperature sensor 9 and a temperature controller 10 (e.g., a microprocessor), each of which are shown in FIG. 1 merely in schematic form and as an example of the components of the fluid temperature control unit 4. In this embodiment, the supply pump 8 works, for example, with a direct current motor and the cooler 7 includes a direct current compressor. Also shown by way of an example are pipelines 11, via which the pump 8 removes the fluid from the fluid container 5 and conveys it to the outside such that it can be used in the hyper/hypothermia system, or via which the fluid is conveyed out of the hyper/hypothermia system back into the fluid container 5. The pump can also be provided in the hyper/hypothermia system such that it can be omitted from the fluid temperature control unit 4 of a temperature control device 1 as according to the invention. Depending on the hyper/hypothermia system in which the temperature control device 1 is used, other components, such as a stirrer for the fluid in the fluid container 5, may be added to (or omitted from) the fluid temperature control unit 4. According to various embodiments, each of the components shown in FIG. 1 may be of the type disclosed in DE 696 34 572 T2, which is hereby incorporated by reference in its entirety.

To supply power to the electrical consuming components, for example, the heater 6, the cooler 7, the supply pump 8 and the temperature controller 10, of the fluid temperature control unit of a temperature control device 1, a power supply unit 12 is provided according to the invention, via which all of the electrical consuming components of the fluid temperature control unit 4 are electrically supplied with constant connected loads irrespective of the local power network. According to embodiments of the invention, direct current is supplied, for example, with a supply voltage of 48 V and a power of up to 3.5 kW. Accordingly, the electrical consuming components of the fluid temperature control unit 4 are supplied via the power supply unit and are, thus, not directly connected to the power network 3. Thus, these components need not be designed for the local power network, but are instead all supplied with direct current by the power supply unit 12. Different electrical consuming components can thereby be supplied with different voltages/powers which are provided by the power supply unit 12 according to the invention. This is indicated in FIG. 1 by the connections between the power supply unit 12 and the fluid temperature control unit 4, which are dashed at one end. The power supply unit 12 thereby performs adaptation to the local power network and conversion to a power supply with constant connected loads.

The power supply unit thus performs any and all necessary conversions to adapt the temperature control device to the conditions of a local or regional power network. The adaptation to the local power network of the region in which the device is to be used is achieved by an appropriate design of the power supply unit, which, on the side facing the connection unit, must be designed for connection to the local power network, but on the side facing the fluid temperature control unit, a uniform power supply with direct current is ensured irrespective of the local power network.

The power supply unit may be any standard power supply (including, for example, switched-mode power supplies) that provides (as standard) one or more of the supply voltages required by the fluid temperature control unit, so that the temperature of the fluid can be controlled. In this way, the fluid temperature control unit is electrically separate from the local power network. As a result, an improved electrical decoupling of the fluid temperature control unit from the power network is achieved, which has a positive effect on use in hyper/hypothermia systems, since network feedback and leakage currents can be reduced. In view of the fact that medical-technical systems such as hyper/hypothermia systems are subject to particularly critical specifications, this decoupling of the fluid temperature control unit from the local power network that is achieved by the power supply unit is advantageous.

Supplying the electrical consuming components of the fluid temperature control unit with direct current enables more precise control during operation, since a precise power control for each individual electrical consuming component can take place, for example, with the aid of inverters. This is true not only for the heater/cooler of the fluid temperature control unit, but also for the pumps which are generally electromotively driven. Overall, the improved controllability of the temperature control device of the invention leads to a reduction of noise in a hyper/hypothermia treatment scenario.

Figure 2:
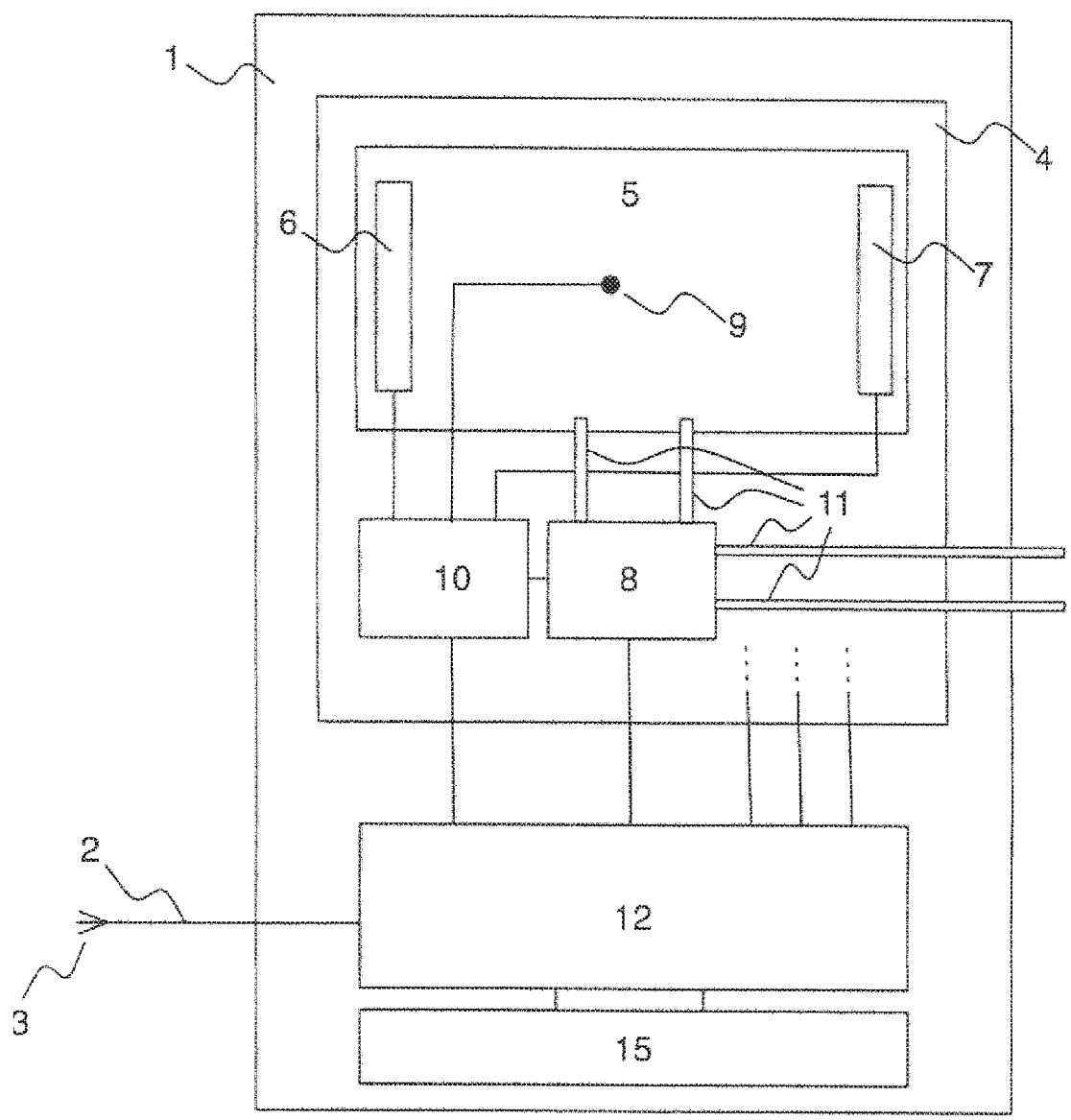
FIG. 2 shows a further embodiment of the temperature control device according to the invention.

FIG. 2 shows further embodiments of a temperature control device 1 according to the invention. As shown in FIG. 2, the control device 1 additionally includes a battery 15 for supplying the electrical consuming components of the fluid temperature control unit 4 with power. The battery 15 is connected to the power supply unit 12 and is charged by this unit when the supply of power occurs via the power network. In this way, the battery 15 can supply power to the power supply unit 12 to ensure delivery of a fail-safe supply of direct current to the electrical consuming components even where the local power network is subject to fluctuations or failure. Thus, designing the temperature control device with direct current electrical consuming components makes it possible to ensure the continuous operation of the temperature control device in a surgical environment.

We claim:

1. A temperature control device for use in fluid-based hyper/hypothermia systems, comprising:
   a connection unit for connecting the device to a local power network; and
   a fluid temperature control unit to heat and/or cool a fluid in a surgical environment during heart surgery including a power supply unit that supplies electrical consuming components of the fluid temperature control unit with direct current and power of up to and including 3500 watts.

2. The temperature control device according to claim 1, wherein the power supply unit is a switched-mode power supply.

3. The temperature control device according to claim 1, wherein the electrical consuming components of the fluid temperature control unit comprise a direct current motor.

4. The temperature control device according to claim 1, wherein the electrical consuming components of the fluid temperature control unit comprise a direct current compressor.

5. The temperature control device according to claim 1, wherein the fluid temperature control unit comprises a battery, the battery being connected to the power supply unit to be charged by the power supply unit when the device is powered by the local power network and to supply direct current to the electrical consuming components of the fluid temperature control unit when the device is not powered by the local power network.

6. A temperature control device for use in fluid-based hyper/hypothermia systems, comprising:
   a connection unit adapted for connecting the device to a local power network;
   a power supply unit that receives an alternating current power from the local power network and converts the alternating current power from the local power network to a direct current power, wherein the power supply unit supplies power of up to and including 3500 watts; and
   a fluid temperature control unit to heat and/or cool a fluid, the fluid temperature control unit including a heater, a cooler, a supply pump, a temperature sensor, and a temperature controller;
   wherein each of the heater, the cooler, the supply pump, and the temperature controller are coupled to the power supply unit and receive the direct current power.

7. The temperature control device according to claim 6, wherein the power supply unit provides a supply voltage of 48 volts.

8. The temperature control device according to claim 6, wherein the fluid temperature control unit comprises a battery, the battery being connected to the power supply unit to be charged by the power supply unit when the device is powered by the local power network and to supply direct current to the heater, the cooler, the supply pump, the temperature sensor and the temperature controller of the fluid temperature control unit when the device is not powered by the local power network.

9. A temperature control device for use in fluid-based hyper/hypothermia systems, comprising:
- a connection unit that connects the temperature control device to a local power network;
- a fluid temperature control unit including a plurality of electrical consuming components, the plurality of electrical consuming components including a pump and a heater and/or cooler for heating and/or cooling a fluid;
- a switched-mode power supply (SMPS) unit connected to the connection unit to receive alternating current power from the local power network, the power supply unit connected to the fluid temperature control unit to supply direct current power to the plurality of electrical consuming components;
- wherein the power supply unit receives an alternating current power from the local power network and converts the alternating current power from the local power network to direct current power;
- wherein the power supply unit provides the direct current power to the pump and the heater and/or cooler, supplying power of up to and including 3500 watts; and
- wherein the fluid temperature control unit is electrically separate from a local power network.

10. The temperature control device according to claim 9, wherein the power supply unit provides a supply voltage of 48 volts.

11. A temperature control device for use in fluid-based hyper/hypothermia systems, comprising:
- a connection unit for connecting the device to any one of a plurality of local power networks providing alternating current power, wherein each of the plurality of local power networks provides alternating current power at a different frequency and/or different voltage;
- a fluid temperature control unit that heats or cools a fluid in a surgical environment during heart surgery including:
  - a fluid container;
  - a heater and/or cooler for heating and/or cooling fluid in the fluid container;
  - a pump that transfers fluid between the fluid container and the fluid-based hyper/hypothermia system; and
- a switched-mode power supply (SMPS) unit that converts the alternating current power from the local power network to a direct current power to supply the heater and/or cooler and the pump of the fluid temperature control unit with direct current power of up to and including 3500 watts, wherein the fluid temperature control unit is electrically separate from a local power network.

12. The temperature control device according to claim 11, wherein the power supply unit supplies a constant connected load of direct current to the heater and/or cooler and the pump of the fluid temperature control unit.

13. The temperature control device according to claim 12, wherein the power supply unit provides a supply voltage of 48 volts.

14. The temperature control device according to claim 11, wherein the fluid temperature control unit includes a temperature controller, wherein the power supply unit supplies direct current power to the temperature controller.

15. The temperature control device according to claim 14, wherein the power supply unit provides different voltages to the heater and/or cooler, the pump, and the temperature controller.

16. The temperature control device according to claim 11, wherein the fluid temperature control unit comprises a battery, the battery being connected to the power supply unit to be charged by the power supply unit when the device is powered by the local power network and to supply direct current to the heater and/or cooler and the pump when the device is not powered by the local power network.

* * * * *